(12) United States Patent
Zinovik et al.

(10) Patent No.: US 11,445,576 B2
(45) Date of Patent: *Sep. 13, 2022

(54) CARTRIDGE WITH A HEATER ASSEMBLY FOR AN AEROSOL-GENERATING SYSTEM

(71) Applicant: Philip Morris Products S.A., Neuchatel (CH)

(72) Inventors: Ihar Zinovik; Oleg Mironov, Neuchatel (CH); Keethan Dasnavis Fernando, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/689,431

(22) Filed: Mar. 8, 2022

(65) Prior Publication Data

US 2022/0191975 A1 Jun. 16, 2022

Related U.S. Application Data

(63) Continuation of application No. 17/669,162, filed on Feb. 10, 2022, which is a continuation of application
(Continued)

(30) Foreign Application Priority Data

Feb. 10, 2014 (EP) ..................... 14154552
Feb. 10, 2014 (EP) ..................... 14154553
Feb. 10, 2014 (EP) ..................... 14154554

(51) Int. Cl.
*H05B 3/34* (2006.01)
*H05B 3/14* (2006.01)
(Continued)

(52) U.S. Cl.
CPC ............. *H05B 3/347* (2013.01); *A24F 40/42* (2020.01); *A61M 11/003* (2014.02);
(Continued)

(58) Field of Classification Search
CPC .... A24F 40/42; A61M 11/003; A61M 11/042; A61M 15/0021; A61M 15/0028;
(Continued)

(56) References Cited

U.S. PATENT DOCUMENTS 4,947,874 A 8/1990 Brooks et al.
2004/0035409 A1 2/2004 Harwig et al.
(Continued)

FOREIGN PATENT DOCUMENTS

CN 103932401 A 7/2014
CN 203986095 U 12/2014
(Continued)

OTHER PUBLICATIONS

U.S. Appl. No. 17/669,162, filed Feb. 10, 2022, Ihar Zinovik, et al.
(Continued)

*Primary Examiner* — Phuong T Nguyen
(74) *Attorney, Agent, or Firm* — Oblon, McClelland, Maier & Neustadt, L.L.P.

(57) ABSTRACT

An aerosol-generating system is provided, including: an aerosol-generating device including a power source; and a cartridge removably coupled to the aerosol-generating device, the cartridge including: a liquid storage portion including a housing having an open end and containing a liquid aerosol-forming substrate, a heater assembly at the open end of the housing and including a planar electrical heating element to heat the liquid aerosol-forming substrate to form an aerosol, and a capillary material in contact with the planar electrical heating element and being configured to convey the liquid aerosol-forming substrate to the planar
(Continued)

electrical heating element, the liquid storage portion being at a first side of the heater assembly and an airflow channel being at a second side of the heater assembly, and the power source of the aerosol-generating device is to supply power to the heater assembly.

20 Claims, 7 Drawing Sheets

Related U.S. Application Data

No. 16/877,412, filed on May 18, 2020, now Pat. No. 11,272,581, which is a continuation of application No. 15/117,620, filed as application No. PCT/EP2014/077840 on Dec. 15, 2014, now Pat. No. 10,687,552.

(51) Int. Cl.
| | |
|---|---|
| *B32B 3/26* | (2006.01) |
| *A61M 11/00* | (2006.01) |
| *A61M 15/00* | (2006.01) |
| *A61M 15/06* | (2006.01) |
| *G05D 23/24* | (2006.01) |
| *B32B 27/28* | (2006.01) |
| *B32B 27/12* | (2006.01) |
| *A24F 40/42* | (2020.01) |
| *B32B 5/02* | (2006.01) |
| *B32B 27/06* | (2006.01) |
| *A61M 11/04* | (2006.01) |

(52) U.S. Cl.
CPC ...... *A61M 11/042* (2014.02); *A61M 15/0021* (2014.02); *A61M 15/0028* (2013.01); *A61M 15/06* (2013.01); *B32B 3/266* (2013.01); *B32B 5/024* (2013.01); *B32B 27/06* (2013.01); *B32B 27/12* (2013.01); *B32B 27/281* (2013.01); *G05D 23/2401* (2013.01); *H05B 3/145* (2013.01); *H05B 3/34* (2013.01); *A61M 2205/8206* (2013.01); *A61M 2206/14* (2013.01); *B32B 2250/02* (2013.01); *B32B 2262/106* (2013.01); *B32B 2307/202* (2013.01); *B32B 2457/00* (2013.01); *H05B 2203/015* (2013.01); *H05B 2203/021* (2013.01)

(58) Field of Classification Search
CPC .......... A61M 15/06; A61M 2205/8206; A61M 2206/14; B32B 3/266; B32B 5/024; B32B 27/06; B32B 27/12; B32B 27/281; B32B 2250/02; B32B 2262/106; B32B 2307/202; B32B 2457/00; G05D 23/2401; H05B 3/145; H05B 3/34; H05B 3/347; H05B 2203/015; H05B 2203/021
USPC ........ 219/211, 270; 392/386, 391, 394, 395; 131/273, 328, 329
See application file for complete search history.

(56) References Cited

U.S. PATENT DOCUMENTS

| | | | |
|---|---|---|---|
| 2005/0045179 A1 | 3/2005 | Faison, Jr. et al. | |
| 2005/0133029 A1* | 6/2005 | Nichols ............. | A61M 15/0048 128/200.14 |
| 2007/0267031 A1 | 11/2007 | Hon | |
| 2008/0023003 A1 | 1/2008 | Rosenthal | |
| 2008/0268060 A1 | 10/2008 | Nguyen et al. | |
| 2011/0036346 A1 | 2/2011 | Cohen et al. | |
| 2011/0226236 A1 | 9/2011 | Buchberger | |
| 2011/0265806 A1 | 11/2011 | Alarcon et al. | |
| 2011/0309157 A1 | 12/2011 | Yang et al. | |
| 2012/0260927 A1 | 10/2012 | Liu | |
| 2013/0087160 A1 | 4/2013 | Gherghe | |
| 2013/0212419 A1* | 8/2013 | Hilburn ................. | G06F 1/3203 713/340 |
| 2013/0213419 A1 | 8/2013 | Tucker et al. | |
| 2013/0298905 A1 | 11/2013 | Levin et al. | |
| 2014/0000638 A1* | 1/2014 | Sebastian ................ | A24F 40/50 131/328 |
| 2014/0060524 A1 | 3/2014 | Liu | |
| 2014/0018261 A9 | 7/2014 | Liu | |
| 2014/0305454 A1 | 10/2014 | Rinker et al. | |
| 2015/0053214 A1 | 2/2015 | Alarcon et al. | |
| 2015/0059779 A1 | 3/2015 | Alarcon et al. | |
| 2015/0090279 A1 | 4/2015 | Chen | |
| 2015/0136156 A1 | 5/2015 | Liu | |

FOREIGN PATENT DOCUMENTS

| | | |
|---|---|---|
| CN | 203986096 U | 12/2014 |
| CN | 204070542 U | 1/2015 |
| CN | 204317492 U | 5/2015 |
| EP | 2 641 490 A1 | 9/2013 |
| JP | 2-124082 A | 5/1990 |
| JP | 6-315366 | 11/1994 |
| JP | 2013-507152 A | 3/2013 |
| JP | 2013-524835 A | 6/2013 |
| WO | 2011/042212 A1 | 4/2011 |
| WO | 2011/137453 A2 | 11/2011 |
| WO | 2013/013808 A1 | 1/2013 |
| WO | 2013/045582 A2 | 4/2013 |
| WO | 2013/126777 A2 | 8/2013 |
| WO | 2013/149404 A1 | 10/2013 |
| WO | 2013/159245 A1 | 10/2013 |
| WO | 2015/066127 A1 | 5/2015 |

OTHER PUBLICATIONS

U.S. Appl. No. 16/877,412, filed May 18, 2020, 2020/0275699 A1, Ihar Zinovik, et al.
U.S. Pat. No. 10,687,552, Jun. 23, 2020, 2016/0353801 A1, Ihar Zinovik, et al.
International Search Report and Written Opinion dated Mar. 20, 2015, in PCT/EP2014/077840 filed Dec. 15, 2014.
Japanese Office Action dated Jul. 4, 2019 in Japanese Patent Application No. 2016-549387 (submitting English translation only), 6 pages.
English translation of Indian Office action dated Nov. 21, 2019 in counterpart Indian Application No. 201617022138, (8 pages).
Korean Office Action dated Feb. 23, 2021 in corresponding Korean Patent Application No. 10-2016-7019364 (with English translation), 12 pages.

* cited by examiner

CARTRIDGE WITH A HEATER ASSEMBLY FOR AN AEROSOL-GENERATING SYSTEM

CROSS REFERENCE TO RELATED APPLICATIONS

This application is a continuation of and claims benefit under 35 U.S.C. § 120 to U.S. application Ser. No. 17/669,162, filed Feb. 10, 2022, which is a continuation of and claims benefit under 35 U.S.C. § 120 to U.S. application Ser. No. 16/877,412, filed May 18, 2020 (now U.S. Pat. No. 11,272,581), which is a continuation of and claims benefit under 35 U.S.C. § 120 to U.S. application Ser. No. 15/117,620, filed Aug. 9, 2016 (now U.S. Pat. No. 10,687,552), which is a U.S. national stage of PCT/EP2014/077840, filed on Dec. 15, 2014, which is based upon and claims benefit of priority under 35 U.S.C. § 119 to European Patent Application No. 14154552.5, filed Feb. 10, 2014, European Patent Application No. 14154553.3, filed Feb. 10, 2014, and European Patent Application No. 14154554.1, filed Feb. 10, 2014, the entire contents of each of which are incorporated herein by reference.

TECHNICAL FIELD

The present invention relates to aerosol-generating systems and to a cartridge for aerosol-generating systems that comprises a heater assembly that is suitable for vaporising a liquid. In particular, the invention relates to handheld aerosol-generating systems, such as electrically operated smoking systems. Aspects of the invention relate to a heater element for an aerosol-generating system.

DESCRIPTION OF THE RELATED ART

One type of aerosol-generating system is an electrically operated smoking system. Handheld electrically operated smoking systems consisting of a device portion comprising a battery and control electronics, and a cartridge portion comprising a supply of aerosol-forming substrate, and an electrically operated vapouriser, are known. A cartridge comprising both a supply of aerosol-forming substrate and a vapouriser is sometimes referred to as a "cartomiser". The vapouriser typically comprises a coil of heater wire wound around an elongate wick soaked in liquid aerosol-forming substrate. The cartridge portion typically comprises not only the supply of aerosol-forming substrate and an electrically operated vapouriser, but also a mouthpiece, which the user sucks on in use to draw aerosol into their mouth.

Thus, electrically operated smoking systems that vaporize a liquid by heating to form an aerosol typically comprise a coil of wire that is wrapped around a capillary material that holds the liquid. Electric current passing through the wire causes resistive heating of the wire which vaporises the liquid in the capillary material. The capillary material is typically held within an airflow path so that air is drawn past the wick and entrains the vapour. The vapour subsequently cools to form an aerosol.

This type of system can be effective at producing aerosol but it can also be challenging to manufacture in a low cost and repeatable way. Furthermore, the wick and coil assembly, together with associated electrical connections, can be fragile and difficult to handle.

Alternatively, systems such as those proposed in US 204/020454, use rectangular cartridges having sheet-like composites that include an integrally formed wick and heating element have been proposed. Such systems require filing of the cartridge through a hole. Integrally forming the wick and heating element introduces additional complexity into the manufacturing process. Moreover, it is desirable to overcome the need to fill a rectangular shaped cartridge through a hole as this introduces additional complexity to the manufacturing of the completed cartridge.

SUMMARY

It would be desirable to provide a heater assembly suitable for an aerosol-generating system, such as a handheld electrically operated smoking system, that is more inexpensive to produce and is robust. It would be further desirable to provide a heater assembly that is as efficient or more efficient than prior heater assemblies in aerosol-generating systems.

In one aspect there is provided a cartridge for use in an electrically operated aerosol-generating system, comprising: a liquid storage portion comprising a housing for holding a liquid aerosol-forming substrate, the housing having an opening; and a heater assembly comprising at least one heater element fixed to the housing and extending across the opening of the housing, wherein the at least one heater element of the heater assembly has a width that is smaller than a width of the opening of the housing.

BRIEF DESCRIPTION OF THE DRAWINGS

Embodiments of the invention will now be described, by way of example only, with reference to the accompanying drawings, in which.

DETAILED DESCRIPTION

The opening of the cartridge has a width and a length dimension. The at least one heater element extends across the full length dimension of the opening of the housing. The width dimension is the dimension perpendicular to the length dimension in the plane of the opening. Preferably the at least one heater element of the heater assembly has a width that is smaller than the width of the opening of the housing.

Preferably a part of the heater element is spaced apart from the perimeter of the opening. Where the heater element comprises a strip attached to the housing at each end, preferably the sides of the strip do not contact the housing. Preferably there is a space between the sides of the strip and the perimeter of the opening.

The width of the heater element may be less than the width of the opening in at least a region of the opening. The width of the heater element may be less than the width of the opening in all of the opening.

The width of the at least one heater element of the heater assembly may be less than 90%, for example less than 50%, for example less than 30%, for example less than 25% of the width of the opening of the housing.

The area of the heater element may be less than 90%, for example less than 50%, for example less than 30%, for example less than 25% of the area of the opening of the housing. The area of the heater elements of the heater assembly may be for example between 10% and 50% of the area of the opening, preferably between 15 and 25% of the area of the opening.

The heater element preferably is supported on an electrically insulating substrate. The insulating substrate preferably has an aperture defining the opening of the housing. The opening may be of any appropriate shape. For example the opening may have a circular, square or rectangular shape. The area of the opening may be small, preferably less than or equal to about 25 mm$^2$.

The at least one heater element is preferably arranged in such a way that the physical contact area with the substrate is reduced compared with a case in which the heater elements of the heater assembly is in contact around the whole of the periphery of the opening. The at least one heater element preferably does not directly contact the perimeter window side walls of the opening. In this way thermal contact to the substrate is reduced and heat losses to the substrate and further adjacent elements of the aerosol-generating system are reduced.

Without wishing to be bound by any particular theory, it is believed that by spacing the heater element away from the housing opening, less heat is transferred to the housing, thus increasing efficiency of heating and therefore aerosol generation. It is also thought that where the heating element is close to or in contact with the periphery of the opening, there is heating of liquid which is located away from the opening. This heating is thought to lead to inefficiency because such heated liquid away from the opening is not able to be utilised in the formation of the aerosol. By spacing the heating element away from the periphery of the opening in the housing, more efficient heating of the liquid, or production of the aerosol may be obtainable.

The spacing between the heater element and the opening periphery is preferably dimensioned such that the thermal contact is significantly reduced. The spacing between the heater element and the opening periphery may be between 25 and 40 microns.

The aerosol generating system may be an electrically operated smoking system.

The substrate preferably comprises at least first and second electrically conductive contact portions for contacting the at least one heater element, the first and second electrically conductive contact portions positioned on opposing sides of the opening to one another, wherein the first and second electrically conductive contact portions are configured to allow contact with an external power supply.

The heater assembly may comprise a plurality of heater elements electrically connected in series. The first and second electrically conductive contact portions may be arranged such that the first contact portion contacts the first heater element and the second contact portion contacts the last heater element of the serially connected heater elements. Additional contact portions are provided at the heater assembly to allow for serial connection of all heater elements. Preferably these additional contact portions are provided at each side of the opening of the substrate.

Preferably, where the heater assembly includes a plurality of heater elements, the heater elements are spatially arranged substantially in parallel to each other. Preferably the heater elements are spaced apart from each other. Without wishing to be bound by any particular theory, it is thought that spacing the heater elements apart from each other may give more efficient heating. By appropriate spacing of the heater elements for example, a more even heating across the area of the opening may be obtained compared with for example where a single heating element having the same area is used.

In a particular preferred embodiment, the heater assembly comprises an odd number of heater elements, preferably three or five heater elements, and the first and second contact portions are located on opposite sides of the aperture of the substrate. This arrangement has the advantage that the first and second contact portions are arranged on opposite sides of the aperture.

The heater assembly may alternatively comprise an even number of heater elements, preferably two or four heater elements. In this embodiment the contact portions are preferably located on the same side of the cartridge. With this arrangement a rather compact design of the electric connection of the heater assembly to the power source may be achieved.

The at least one heater element may each be formed from a plurality of electrically conductive filaments, which may form a mesh or array of filaments or may comprise a woven or non-woven fabric. The heater element may be fluid permeable.

In some examples, the at least one heater element has a first face that is fixed to the electrically insulating substrate and the first and second electrically conductive contact portions are configured to allow contact with an external power supply on a second face of the heater element opposite to the first face.

The system may further comprise a liquid storage portion comprising a housing containing a liquid aerosol-forming substrate, wherein the heater assembly is fixed to the housing of the liquid storage portion. The housing may be a rigid housing and impermeable to fluid. As used herein "rigid housing" means a housing that is self-supporting. The rigid housing of the liquid storage portion preferably provides mechanical support to the heater assembly.

The liquid storage portion may comprise a capillary material configured to convey liquid aerosol-forming substrate to the heater assembly.

The provision of a heater assembly of this type in an aerosol-generating system has several advantages over a conventional wick and coil arrangement. A heater element comprising a mesh or array of filaments allows for a greater area of the heater to be in contact with a liquid being vaporized. The heater assembly can be inexpensively produced, using readily available materials and using mass production techniques. The heater assembly is robust allowing it to be handled and fixed to other parts of the aerosol-generating system during manufacture, and in particular to form part of a removable cartridge. The provision of electrically conductive contact portions forming part of the heater element allows for reliable and simple connection of the heater assembly to a power supply.

The electrically conductive filaments may be substantially flat. As used herein, "substantially flat" preferably means formed in a single plane and for example not wrapped around or other conformed to fit a curved or other non-planar shape. A flat heater assembly can be easily handled during manufacture and provides for a robust construction.

The heater element or heater assembly may be substantially flat.

The at least one heater element may comprise a mesh having interstices between the electrically conductive filaments.

In such an arrangement, preferably at least a portion of the heater element is spaced apart from the periphery of the opening by a distance which is greater than a dimension of the interstices of that portion of the heater element.

The electrically conductive filaments may define interstices between the filaments and the interstices may have a width of between 10 μm and 100 μm. Preferably the filaments give rise to capillary action in the interstices, so that in use, liquid to be vaporized is drawn into the interstices, increasing the contact area between the heater assembly and the liquid.

The electrically conductive filaments may form a mesh of size between 160 and 600 Mesh US (+/−10%) (i.e. between 160 and 600 filaments per inch (+/−10%)). The width of the interstices is preferably between 75 μm and 25 μm. The percentage of open area of the mesh, which is the ration of the area of the interstices to the total area of the mesh is preferably between 25 and 56%. The mesh may be formed using different types of weave or lattice structures. Alternatively, the electrically conductive filaments consist of an array of filaments arranged parallel to one another.

The mesh, array or fabric of electrically conductive filaments may also be characterised by its ability to retain liquid, as is well understood in the art.

The electrically conductive filaments may have a diameter of between 8 μm and 100 μm, preferably between 8 μm and 50 μm, and more preferably between 8 μm and 39 μm. The filaments may have a round cross section or may have for example a flattened cross section.

The area of the mesh, array or fabric of electrically conductive filaments of a single heater element may be small, preferably less than or equal to 25 mm$^2$, allowing it to be incorporated in to a handheld system. The heater element may, for example, be rectangular and have a length of about 5 mm and a width of about 2 mm. In some examples, the width is below 2 mm, for example the width is about 1 mm. The smaller the width of the heater elements, the more heater elements may be connected in series in the heater assembly of the present invention. An advantage of using smaller width heater elements that are connected in series is that the electric resistance of the combination of heater elements is increased.

The heater element may cover an area of between 10% and 50% of the area of the heater assembly. The mesh or array of electrically conductive filaments covers an area of between 15 and 25% of the area of the heater assembly.

The electrically conductive filaments may comprise any suitable electrically conductive material. Suitable materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, constantan, nickel-, cobalt-, chromium-, aluminium-titanium-zirconium-, hafnium-, niobium-, molybdenum-, tantalum-, tungsten-, tin-, gallium-, manganese- and iron-containing alloys, and super-alloys based on nickel, iron, cobalt, stainless steel, Timetal®, iron-aluminium based alloys and iron-manganese-aluminium based alloys. Timetal® is a registered trade mark of Titanium Metals Corporation. The filaments may be coated with one or more insulators. Preferred materials for the electrically conductive filaments are 304, 316, 304L, and 316L stainless steel, and graphite.

The electrical resistance of the mesh, array or fabric of electrically conductive filaments of the heater element is preferably between 0.3 and 4 Ohms. More preferably, the electrical resistance of the mesh, array or fabric of electrically conductive filaments is between 0.5 and 3 Ohms, and more preferably about 1 Ohm. The electrical resistance of the mesh, array or fabric of electrically conductive filaments is preferably at least an order of magnitude, and more preferably at least two orders of magnitude, greater than the electrical resistance of the contact portions. This ensures that the heat generated by passing current through the heater element is localised to the mesh or array of electrically conductive filaments. It is generally advantageous to have a low overall resistance for the heater element if the system is powered by a battery. Minimizing parasitic losses between the electrical contacts and the mesh or the filaments is also desirable to minimize parasitic power losses. A low resistance, high current system allows for the delivery of high power to the heater element. This allows the heater element to heat the electrically conductive filaments to a desired temperature quickly.

The electrically conductive contact portions may be fixed directly to the electrically conductive filaments. The contact portions may be positioned between the electrically conductive filaments and the electrically insulating substrate. For example, the contact portions may be formed from a copper foil that is plated onto the insulating substrate. The contact portions may also bond more readily with the filaments than the insulating substrate would.

Alternatively, the electrically conductive contact portions may be integral with the electrically conductive filaments of the heater elements. For example, the heater element may be formed by etching a conductive sheet to provide a plurality of filaments between two contact portions.

At least one heater element of the heater assembly may comprise at least one filament made from a first material and at least one filament made from a second material different from the first material. This may be beneficial for electrical or mechanical reasons. For example, one or more of the filaments may be formed from a material having a resistance that varies significantly with temperature, such as an iron aluminium alloy. This allows a measure of resistance of the filaments to be used to determine temperature or changes in temperature. This can be used in a puff detection system and for controlling heater temperature to keep it within a desired temperature range.

The electrically insulating substrate may comprise any suitable material, and is preferably a material that is able to tolerate high temperatures (in excess of 300 degree Celsius) and rapid temperature changes. An example of a suitable material is a polyimide film, such as Kapton®.

The aerosol-forming substrate is a substrate capable of releasing volatile compounds that can form an aerosol. The volatile compounds may be released by heating the aerosol-forming substrate.

The aerosol-forming substrate may comprise plant-based material. The aerosol-forming substrate may comprise tobacco. The aerosol-forming substrate may comprise a tobacco-containing material containing volatile tobacco flavour compounds, which are released from the aerosol-forming substrate upon heating. The aerosol-forming substrate may alternatively comprise a non-tobacco-containing material. The aerosol-forming substrate may comprise homogenised plant-based material. The aerosol-forming substrate may comprise homogenised tobacco material. The aerosol-forming substrate may comprise at least one aerosol-former. An aerosol-former is any suitable known compound or mixture of compounds that, in use, facilitates formation of a dense and stable aerosol and that is substantially resistant to thermal degradation at the operating temperature of operation of the system. Suitable aerosol-formers are well known in the art and include, but are not limited to: polyhydric alcohols, such as triethylene glycol, 1,3-butanediol and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate. Preferred aerosol formers are polyhydric alcohols or mixtures thereof, such as triethylene glycol, 1,3-butanediol and, most preferred, glycerine. The aerosol-forming substrate may comprise other additives and ingredients, such as flavourants.

The housing of the liquid storage portion may contain a capillary material and the capillary material may extend into the interstices between the filaments.

The capillary material may have a fibrous or spongy structure. The capillary material preferably comprises a bundle of capillaries. For example, the capillary material may comprise a plurality of fibres or threads or other fine bore tubes. The fibres or threads may be generally aligned to convey liquid to the heater. Alternatively, the capillary material may comprise sponge-like or foam-like material. The structure of the capillary material forms a plurality of small bores or tubes, through which the liquid can be transported by capillary action. The capillary material may comprise any suitable material or combination of materials. Examples of suitable materials are a sponge or foam material, ceramic- or graphite-based materials in the form of fibres or sintered powders, foamed metal or plastics material, a fibrous material, for example made of spun or extruded fibres, such as cellulose acetate, polyester, or bonded polyolefin, polyethylene, terylene or polypropylene fibres, nylon fibres or ceramic. The capillary material may have any suitable capillarity and porosity so as to be used with different liquid physical properties. The liquid has physical properties, including but not limited to viscosity, surface tension, density, thermal conductivity, boiling point and vapour pressure, which allow the liquid to be transported through the capillary device by capillary action.

The capillary material may be in contact with the electrically conductive filaments. The capillary material may extend into interstices between the filaments. The heater assembly may draw liquid aerosol-forming substrate into the interstices by capillary action. The capillary material may be in contact with the electrically conductive filaments over substantially the entire extent of the aperture.

The housing may contain two or more different capillary materials, wherein a first capillary material, in contact with the heater element, has a higher thermal decomposition temperature and a second capillary material, in contact with the first capillary material but not in contact with the heater element has a lower thermal decomposition temperature. The first capillary material effectively acts as a spacer separating the heater element from the second capillary material so that the second capillary material is not exposed to temperatures above its thermal decomposition temperature. As used herein, "thermal decomposition temperature" means the temperature at which a material begins to decompose and lose mass by generation of gaseous by products. The second capillary material may advantageously occupy a greater volume than the first capillary material and may hold more aerosol-forming substrate that the first capillary material. The second capillary material may have superior wicking performance to the first capillary material. The second capillary material may be a less expensive or have a higher filling capability than the first capillary material. The second capillary material may be polypropylene.

The first capillary material may separate the heater assembly from the second capillary material by a distance of at least 1.5 mm, and preferably between 1.5 and 2 mm in order to provide a sufficient temperature drop across the first capillary material.

The liquid storage portion may be positioned on a first side of the electrically conductive filaments and an airflow channel positioned on an opposite side of the electrically conductive filaments to the liquid storage portion, such that air flow past the electrically conductive filaments entrains vapourised liquid aerosol-forming substrate.

The system may further comprise electric circuitry connected to the heater element and to an electrical power source, the electric circuitry configured to monitor the electrical resistance of the heater element or of one or more filaments of the heater element, and to control the supply of power to the heater element from the power source dependent on the electrical resistance of the heater element or specifically the electrical resistance of the one or more filaments.

The electric circuitry may comprise a microprocessor, which may be a programmable microprocessor, a microcontroller, or an application specific integrated chip (ASIC) or other electronic circuitry capable of providing control. The electric circuitry may comprise further electronic components. The electric circuitry may be configured to regulate a supply of power to the heater. Power may be supplied to the heater element continuously following activation of the system or may be supplied intermittently, such as on a puff by puff basis. The power may be supplied to the heater element in the form of pulses of electrical current.

The system advantageously comprises a power supply, typically a battery such as a lithium iron phosphate battery, within the main body of the housing. As an alternative, the power supply may be another form of charge storage device such as a capacitor. The power supply may require recharging and may have a capacity that allows for the storage of enough energy for one or more smoking experiences. For example, the power supply may have sufficient capacity to allow for the continuous generation of aerosol for a period of around six minutes, corresponding to the typical time taken to smoke a conventional cigarette, or for a period that is a multiple of six minutes. In another example, the power supply may have sufficient capacity to allow for a predetermined number of puffs or discrete activations of the heater.

The system may comprise a main unit and a cartridge that is removably coupled to the main unit, wherein the liquid storage portion and heater assembly are provided in the cartridge and the main unit comprises a power supply. As used herein, the cartridge being "removably coupled" to the device means that the cartridge and device can be coupled and uncoupled from one another without significantly damaging either the device or the cartridge.

The system may be an electrically operated smoking system. The system may be a handheld aerosol-generating system. The aerosol-generating system may have a size comparable to a conventional cigar or cigarette. The smoking system may have a total length between approximately 30 mm and approximately 150 mm. The smoking system may have an external diameter between approximately 5 mm and approximately 30 mm.

The electrically insulating substrate may be a flexible sheet material. The electrically conductive contact portions and electrically conductive filaments may be integrally formed with one another.

As used herein, "electrically conductive" means formed from a material having a resistivity of $1\times10^{-4}$ Ωm, or less. As used herein, "electrically insulating" means formed from a material having a resistivity of $1\times10^{4}$ Ωm or more.

The present invention is also directed to an aerosol-generating system, preferably an electrically operated smoking system, comprising a cartridge according to the present invention.

The aerosol-generating system further comprises a main unit, to which the cartridge is removably coupled. The liquid storage portion and the heater assembly are provided in the cartridge and the main unit comprises a power supply. Different arrangements are possible.

The cartridge can be exchanged after consumption. As the cartridge holds the liquid and the heater assembly, the heater assembly is also exchanged regularly such that the optimal vaporization conditions are maintained even after longer use of the main unit.

The aerosol-generating system preferably further comprises electric circuitry connected to the heater assembly and to an electrical power source. The electric circuitry is configured to monitor the electrical resistance of the heater assembly or of one or more filaments of a heater element of the heater assembly, and to control a supply of power from the electrical power source to the heater assembly dependent on the electrical resistance of the heater assembly or the one or more filaments. By monitoring the temperature of the heater element, the system can prevent over- or under-heating of the heater assembly and ensure that optimal vaporization conditions are provided.

The present invention is also directed to a method of manufacture of a cartridge for use in an aerosol-generating system, for example an electrically operated aerosol-generating system, comprising the steps of providing a liquid storage portion with a housing having an opening, filling the liquid storage portion with liquid aerosol-forming substrate and providing a heater assembly comprising at least one heater element extending across the opening of the housing wherein the heater element is smaller than the opening. The width of the at least one heater element of the heater assembly may be less than 90%, preferably less than 50, further preferably less than 30%, most preferably less than 25% of the width of the opening of the housing.

The heater assembly and the heater element or elements are preferably fluid permeable. As used herein "fluid permeable" in relation to a heater assembly means that the aerosol-forming substrate, in a gaseous phase and possibly in a liquid phase, can readily pass through the heater assembly or heater element.

The term "substantially flat" filament arrangement is used to refer to a filament arrangement that is preferably in the form of a substantially two dimensional topological manifold. Thus, the substantially flat filament arrangement extends in two dimensions along a surface substantially more than in a third dimension. In particular, the dimensions of the substantially flat filament arrangement in the two dimensions within the surface are at least 5 times larger than in the third dimension, normal to the surface. An example of a substantially flat filament arrangement is a structure between two substantially parallel surfaces, wherein the distance between these two surfaces is substantially smaller than the extension within the surfaces. In some embodiments, the substantially flat filament arrangement is planar. In other embodiments, the substantially flat filament arrangement is curved along one or more dimensions, for example forming a dome shape or bridge shape.

The term "filament" is used preferably to refer to an electrical path arranged between two electrical contacts. A filament may arbitrarily branch off and diverge into several paths or filaments, respectively, or may converge from several electrical paths into one path. A filament may have a round, square, flat or any other form of cross-section. A filament may be arranged in a straight or curved manner.

The term "filament arrangement" is used preferably to refer to an arrangement of one or preferably a plurality of filaments. The filament arrangement may be an array of filaments, for example arranged parallel to each other. Preferably, the filaments may form a mesh. The mesh may be woven or non-woven.

Figures 1A, 1B:
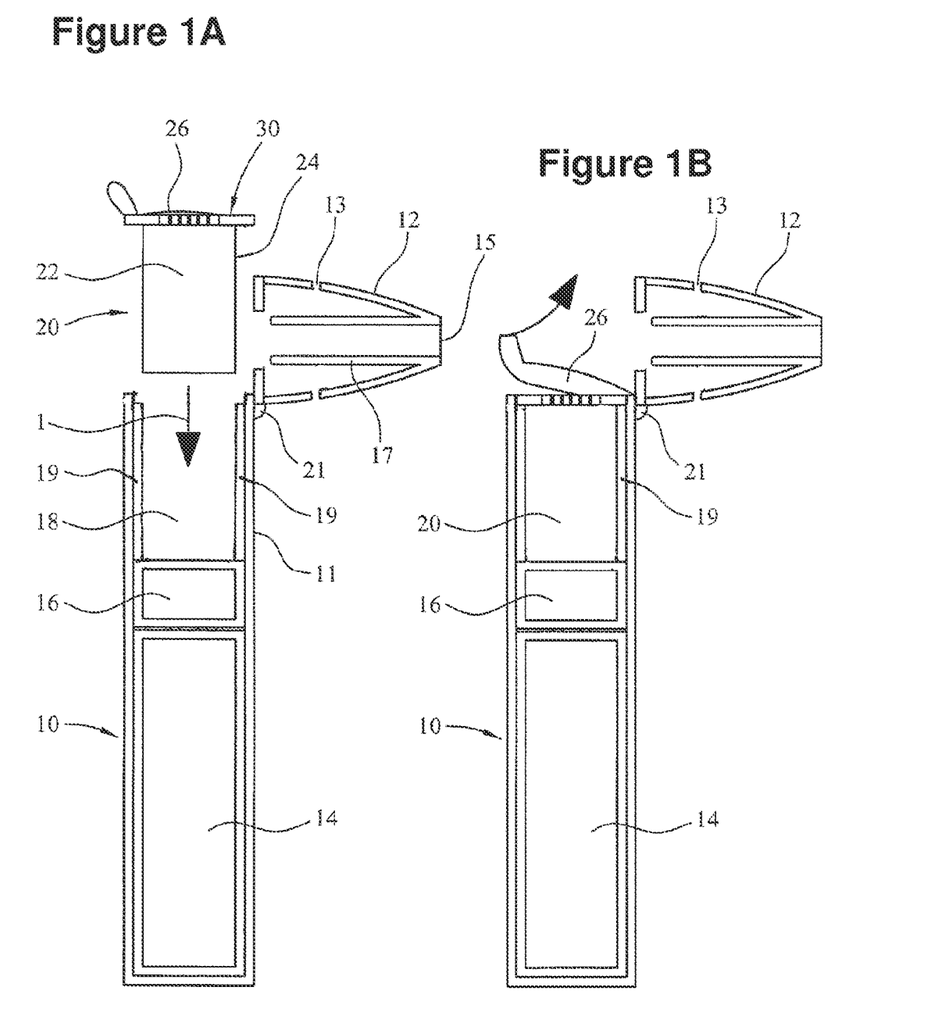
FIGS. 1A to 1D are schematic illustrations of a system, incorporating a cartridge, in accordance with an embodiment of the invention.

FIGS. 1A to 1D are schematic illustrations of an aerosol-generating system, including a cartridge in accordance with an embodiment of the invention. FIG. 1A is a schematic view of an aerosol-generating device 10 and a separate cartridge 20, which together form the aerosol-generating system. In this example, the aerosol-generating system is an electrically operated smoking system.

The cartridge 20 contains an aerosol-forming substrate and is configured to be received in a cavity 18 within the device. Cartridge 20 should be replaceable by a user when the aerosol-forming substrate provided in the cartridge is depleted. FIG. 1A shows the cartridge 20 just prior to insertion into the device, with the arrow 1 in FIG. 1A indicating the direction of insertion of the cartridge.

Figure 1C:
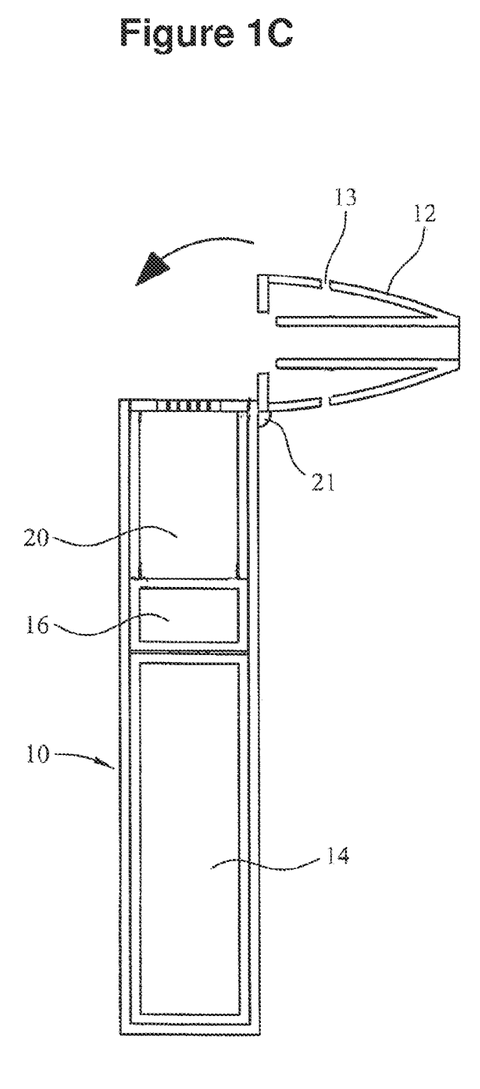
Figure 1D:
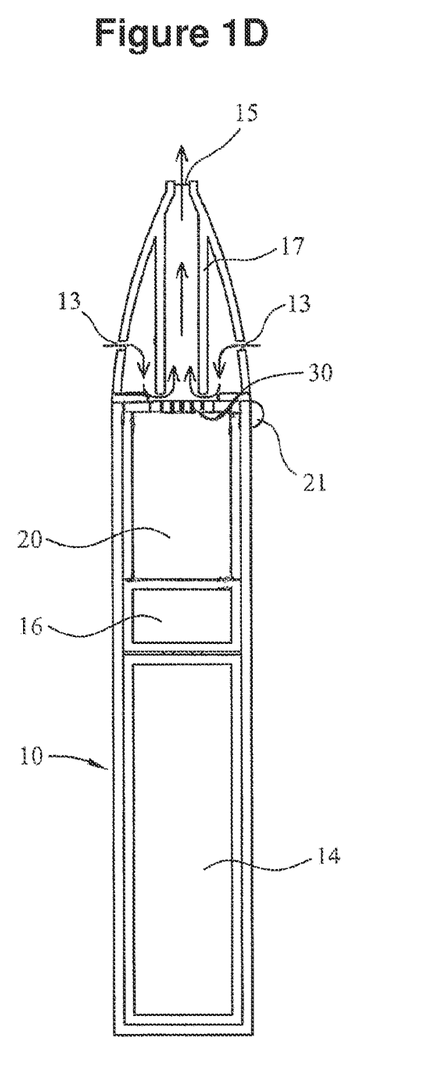

The aerosol-generating device 10 is portable and has a size comparable to a conventional cigar or cigarette. The device 10 comprises a main body 11 and a mouthpiece portion 12. The main body 11 contains a battery 14, such as a lithium iron phosphate battery, control electronics 16 and a cavity 18. The mouthpiece portion 12 is connected to the main body 11 by a hinged connection 21 and can move between an open position as shown in FIG. 1C and a closed position as shown in FIG. 1D. The mouthpiece portion 12 is placed in the open position to allow for insertion and removal of cartridges 20 and is placed in the closed position when the system is to be used to generate aerosol, as will be described. The mouthpiece portion comprises a plurality of air inlets 13 and an outlet 15. In use, a user sucks or puffs on the outlet to draw air from the air inlets 13, through the mouthpiece portion to the outlet 15, and thereafter into the mouth or lungs of the user. Internal baffles 17 are provided to force the air flowing through the mouthpiece portion 12 past the cartridge, as will be described.

The cavity 18 has a circular cross-section and is sized to receive a housing 24 of the cartridge 20. Electrical connectors 19 are provided at the sides of the cavity 18 to provide an electrical connection between the control electronics 16 and battery 14 and corresponding electrical contacts on the cartridge 20.

FIG. 1B shows the system of FIG. 1A with the cartridge inserted into the cavity 18, and the cover 26 being removed. In this position, the electrical connectors rest against the electrical contacts on the cartridge, as will be described.

FIG. 1C shows the system of FIG. 1B with the cover 26 fully removed and the mouthpiece portion 12 being moved to a closed position.

FIG. 1D shows the system of FIG. 1C with the mouthpiece portion 12 in the closed position. The mouthpiece portion 12 is retained in the closed position by a clasp mechanism, as is schematically illustrated in FIG. 1D. FIG. 1D illustrates the main body 11 and mouthpiece portion 12 connected by hinged connection 21. It will be apparent to a person of ordinary skill in the art that other suitable mechanisms for retaining the mouthpiece in a closed position may be used, such as a snap fitting or a magnetic closure.

The mouthpiece portion 12 in a closed position retains the cartridge in electrical contact with the electrical connectors 19 so that a good electrical connection is maintained in use, whatever the orientation of the system is. The mouthpiece portion 12 may include an annular elastomeric element that engages a surface of the cartridge and is compressed between a rigid mouthpiece housing element and the cartridge when the mouthpiece portion 12 is in the closed position. This ensures that a good electrical connection is maintained despite manufacturing tolerances.

Of course other mechanisms for maintaining a good electrical connection between the cartridge and the device may, alternatively or in addition, be employed. For example, the housing 24 of the cartridge 20 may be provided with a thread or groove (not illustrated) that engages a corresponding groove or thread (not illustrated) formed in the wall of the cavity 18. A threaded engagement between the cartridge and device can be used to ensure the correct rotational alignment as well as retaining the cartridge in the cavity and ensuring a good electrical connection. The threaded connection may extend for only half a turn or less of the cartridge, or may extend for several turns. Alternatively, or in addition, the electrical connectors 19 may be biased into contact with the contacts on the cartridge.

Figure 2A:
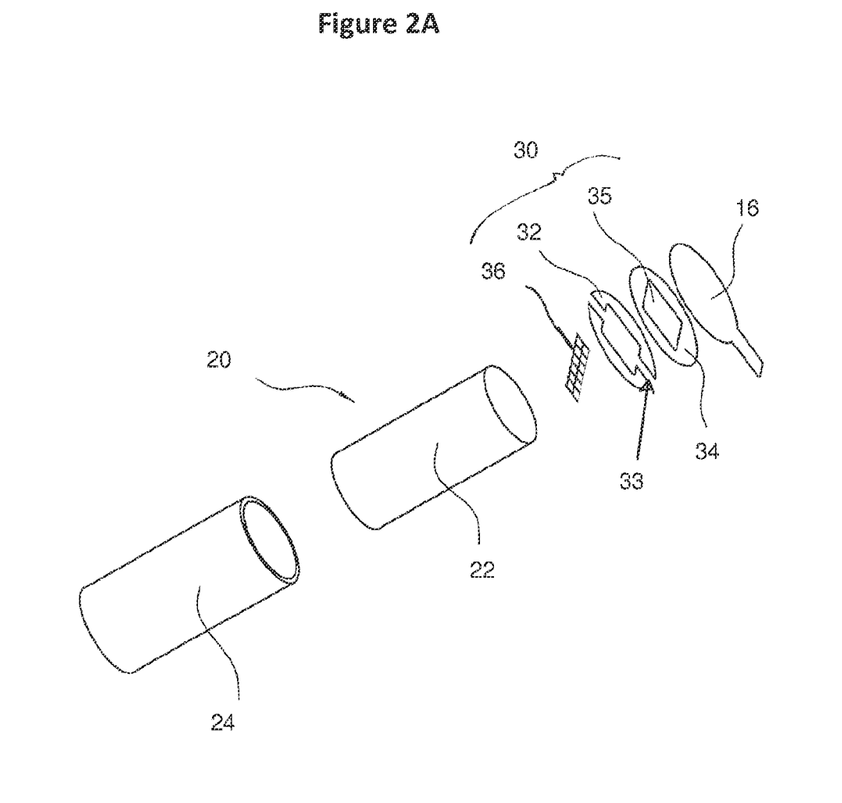
FIGS. 2A and 2B are exploded views of an example cartridge of a system shown in FIGS. 1A to 1D.
Figure 2B:
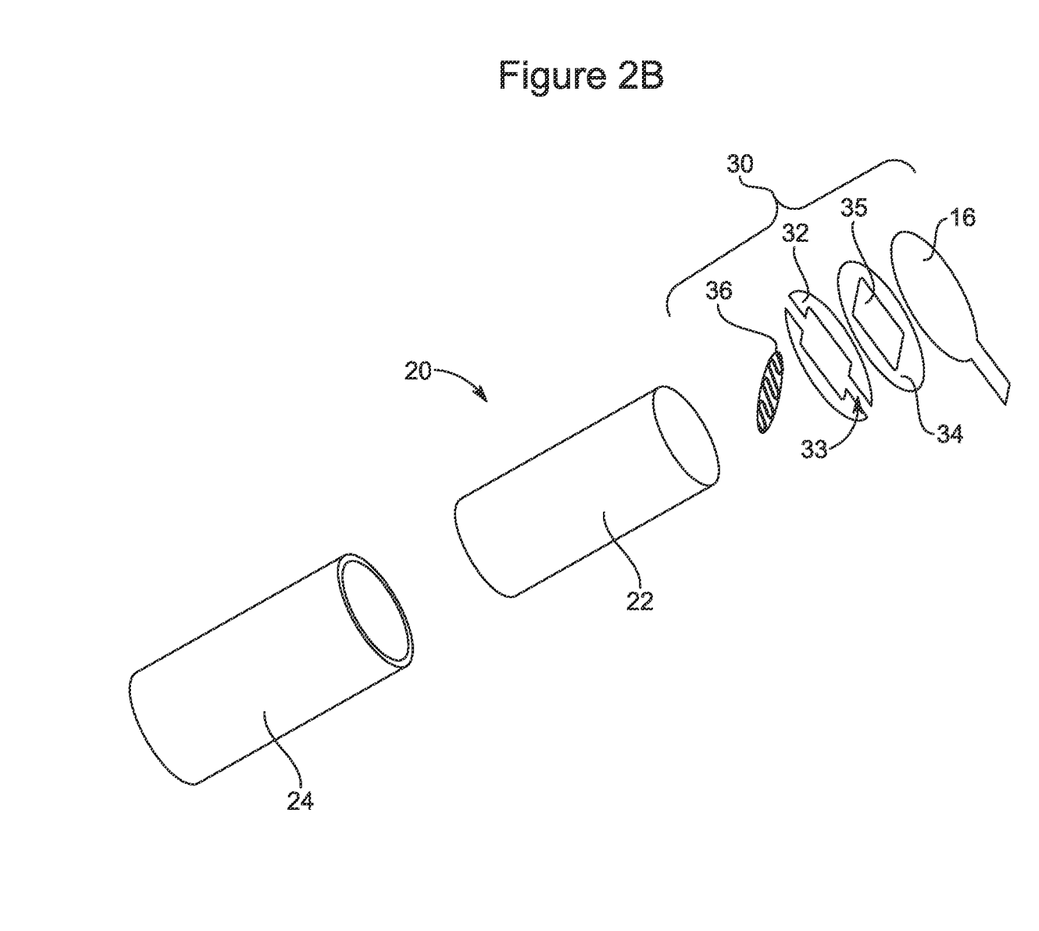

FIGS. 2A and 2B are exploded views of a cartridge 20 suitable for use in an aerosol-generating system, for example an aerosol-generating system of the type of FIGS. 1A-1D. As shown in FIGS. 2A and 2B, cartridge 20 comprises a generally circular cylindrical housing 24 that has a size and shape selected to be received into a corresponding cavity of, or mounted in an appropriate way with other elements of the aerosol-generating system, for example cavity 18 of the system of FIGS. 1A-1D. The housing 22 contains a capillary material 22 that is soaked in a liquid aerosol-forming substrate. In this example the aerosol-forming substrate comprises 39% by weight glycerine, 39% by weight propylene glycol, 20% by weight water and flavourings, and 2% by weight nicotine. A capillary material is a material that actively conveys liquid from one end to another, and may be made from any suitable material. In this example the capillary material is formed from polyester.

The housing 22 has an open end to which a heater assembly 30 is fixed. The heater assembly 30 comprises a substrate 34 having an aperture 35 formed in it, a pair of electrical contacts 32 fixed to the substrate and separated from each other by a gap 33, and a heater element 36 formed from a mesh of electrically conductive heater filaments (as shown in FIG. 2A) or an electrical heating element arranged in a curved manner (as shown in FIG. 2B), spanning the aperture 35 and fixed to the electrical contacts 32 on opposite sides of the aperture 35.

The heater assembly 30 is covered by a removable cover 26. The cover 26 comprises a liquid impermeable plastic sheet that is glued to the heater assembly but which can be easily peeled off. A tab is provided on the side of the cover 26 to allow a user to grasp the cover when peeling it off. It will now be apparent to one of ordinary skill in the art that although gluing is described as the method to a secure the impermeable plastic sheet to the heater assembly 30, other methods familiar to those in the art may also be used including heat sealing or ultrasonic welding, so long as the cover 26 may easily be removed by a consumer.

It will be understood that other cartridge designs are possible. For example, the capillary material with the cartridge may comprise two or more separate capillary materials, or the cartridge may comprise a tank for holding a reservoir of free liquid.

The heater element 36 (e.g., the mesh of filaments as shown in FIG. 2A, or the electrical heating element arranged in a curved manner as shown in FIG. 2B) are exposed through the aperture in the substrate 34 so that vapourised aerosol-forming substrate can escape into the airflow past the heater assembly.

In use, the cartridge 20 is placed in the aerosol-generating system, and the heater assembly 30 is contacted to a power source comprised in the aerosol-generating system. An electronic circuitry is provided to power the heater element 36 and to volatilize the aerosol-generating substrate.

Figure 3:
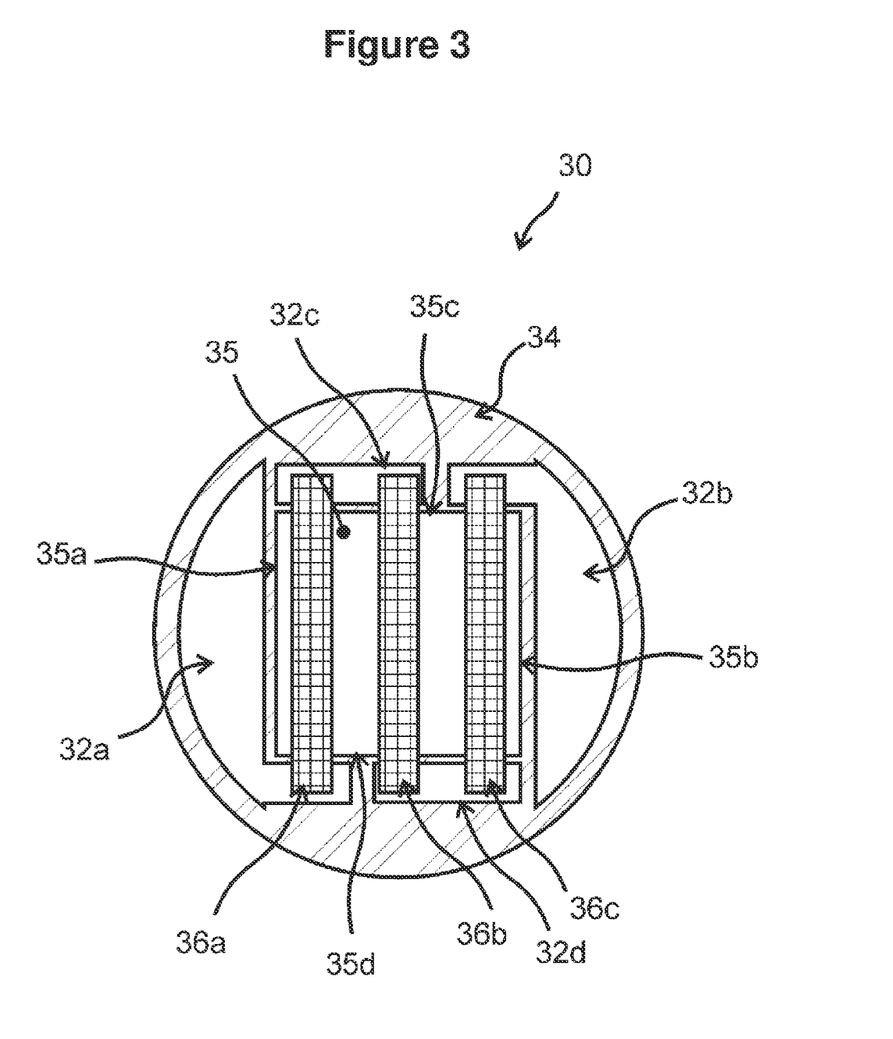
FIG. 3 shows a heater assembly with three heater elements.

In FIG. 3 an example of the heater assembly 30 of the present invention is depicted, in which three substantially parallel heater elements 36a, 36b, 36c are electrically connected in series. The heater assembly 30 comprises an electrically insulating substrate 34 having a square aperture 35 formed in it. The size of the aperture is 5 mm×5 mm in this example, although it will be appreciated that other shapes and sizes of aperture could be used as appropriate for the particular application of the heater. A first and a second electrical contact 32a, 32b are provided at opposite sides of the aperture 35 and extend substantially parallel to the side edges 35a, 35b of the aperture 35. Two additional contacts 32c, 32d are provided adjacent parts of opposing side edges 35c, 35d of the aperture 35. The first heater element is connected between the first contact portion 32a and the additional contact portion 32c. The second heater element 36b is connected between additional contact portion 32c and additional contact portion 32d. The third heater element 36c is connected between additional contact portion 32c and the second contact portion 32b. In this embodiment the heater assembly 30 comprises an odd number of heater elements 36, namely three heater elements and the first and second contact portions 32a, 32b are located on opposite sides of the aperture 35 of the substrate 34. Heater elements 36a and 36c are spaced from the side edges 35a, 35c of the aperture such that there is no direct physical contact between these heater elements 36a, 36c and the insulating substrate 34. Without wishing to be bound by any particular theory, it is thought that this arrangement can reduces heat transfer to the insulating substrate 34 and can allow for effective volatilization of the liquid aerosol-generating substrate.

Figure 4:
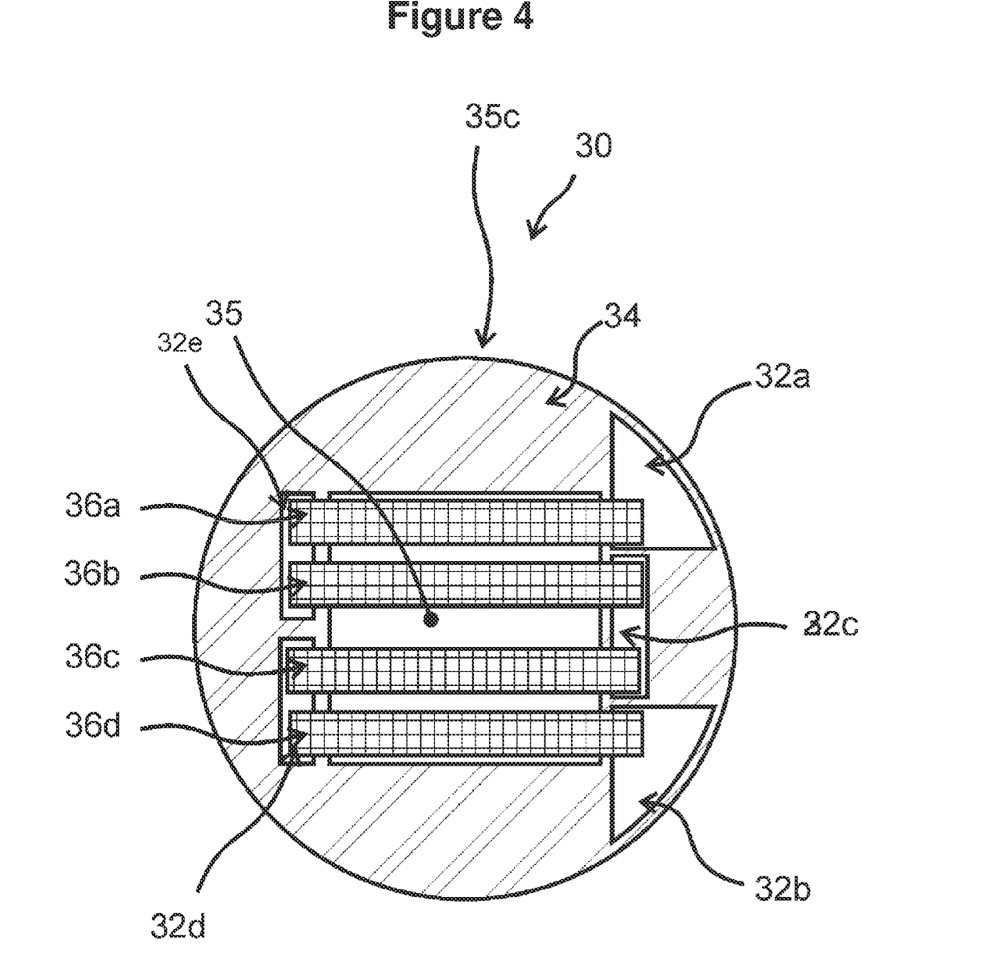
FIG. 4 shows a heater assembly with four heater elements.

In FIG. 4 a further example of the heater assembly 30 of the present invention is depicted, in which four heater elements 36a, 36b, 36c, 36d are electrically connected in series. The heater assembly 30 comprises an electrically insulating substrate 34 having a square aperture 35 formed in it. The size of the aperture is 5 mm×5 mm. A first and a second contact portion 32a, 32b is provided adjacent an upper and lower portion, respectively, of the same side edge 35b of the aperture 35. Three additional contact portions 32c, 32d, 32e are provided, wherein two contact portions are provided adjacent parts of opposing side edge 35a, and one contact portion is provided parallel to side edge 35b between the first and second contact portions 32a, 32b. The four heater elements 36a, 36b, 36c, 36d are connected in series between the these five contact portions 32a, 32c, 32d, 32e, 32b as illustrated in FIG. 4. Again none of the long side edges of the heater elements is in direct physical contact with any of the side edges of the aperture such that again heat transfer to the insulating substrate is reduced.

In this embodiment the heater assembly 30 comprises an even number of heater elements 36, namely four heater elements 36a, 36b, 36c, 36d and the first and second contact portions 32a, 32b are located on the same side of the aperture 35 of the substrate 34.

In arrangements such as that shown in FIGS. 3 and 4, the arrangement of the heater elements may be such that the gap between adjacent heater elements is substantially the same. For example, the heater elements may be regularly spaced across the width of the aperture 35. In other arrangements, different spacings between the heater elements may be used, for example to obtain a desired heating profile. Other shapes of aperture or of the heater elements may be used.

The heater assembly may comprise a mesh formed from 304L stainless steel, with a mesh size of about 400 Mesh US (about 400 filaments per inch). The filaments have a diameter of around 16 μm. The mesh is connected to electrical contacts 32 that are separated from each other by a gap and are formed from a copper foil having a thickness of around 30 μm. The electrical contacts 32 are provided on a polyimide substrate 34 having a thickness of about 120 μm. The filaments forming the mesh define interstices between the filaments. The interstices in this example have a width of around 37 μm, although larger or smaller interstices may be used. Using a mesh of these approximate dimensions allows a meniscus of aerosol-forming substrate to be formed in the interstices, and for the mesh of the heater assembly to draw aerosol-forming substrate by capillary action. The open area of the mesh, i.e. the ratio of the area of interstices to the total area of the mesh is advantageously between 25 and 56%. The total resistance of the heater assembly is around 1 Ohm. The mesh provides the vast majority of this resistance so that the majority of the heat is produced by the mesh. In this example the mesh has an electrical resistance more than 100 times higher than the electrical contacts 32.

The substrate 34 is electrically insulating and, in this example, is formed from a polyimide sheet having a thickness of about 120 μm. The substrate is circular and has a diameter of 8 mm. The mesh is rectangular and in some examples has side lengths of 5 mm and 2 mm. These dimensions allow for a complete system having a size and shape similar to a convention cigarette or cigar to be made. Another example of dimensions that have been found to be effective is a circular substrate of diameter 5 mm and a rectangular mesh of 1 mm×4 mm.

In an alternative, heater assembly in accordance with the disclosure, the mesh 36 can be replaced by an array of parallel electrically conductive filaments. The array of filaments is formed from 304L stainless steel and have a diameter of around 16 μm.

The filaments may be bonded directly to the substrate 34, the contacts 32 then being bonded onto the filaments. The contacts 32 are separated from each other by an insulating gap, and are formed from copper foil of a thickness of around 30 μm. The same arrangement of substrate filaments and contacts can be used for a mesh type heater. Having the contacts as an outermost layer can be beneficial for providing reliable electrical contact with a power supply.

The heater assembly may comprise a plurality of heater filaments that are integrally formed with electrical contacts. Both the filaments and the electrical contacts are formed from a stainless steel foil that is etched to define filaments. The contacts are separated by a gap except when joined by the filaments. The stainless steel foil is provided on a polyimide substrate 34. Again the filaments provide the vast majority of this resistance, so that the majority of the heat is produced by the filaments. In this example the filaments have an electrical resistance more than 100 times higher than the electrical contacts.

In the cartridge shown in FIG. 3, the contacts 32 and filaments 36, 38 are located between the substrate layer 34 and the housing 24. However, it is possible to mount the heater assembly to the cartridge housing the other way up, so that the polyimide substrate is directly adjacent to the housing 24.

Although the embodiments described have cartridges with housings having a substantially circular cross section, it is of course possible to form cartridge housings with other shapes, such as rectangular cross section or triangular cross section. These housing shapes would ensure a desired orientation within the corresponding shaped cavity, to ensure the electrical connection between the device and the cartridge.

The capillary material 22 is advantageously oriented in the housing 24 to convey liquid to the heater assembly 30. When the cartridge is assembled, the heater filaments 36 may be in contact with the capillary material 22 and so aerosol-forming substrate can be conveyed directly to the heater. In examples of the invention, aerosol-forming substrate contacts most of the surface of each filament so that most of the heat generated by the heater assembly passes directly into the aerosol-forming substrate. In contrast, in conventional wick and coil heater assemblies only a small fraction of the heater wire is in contact with the aerosol-forming substrate. The capillary material 27 may extend into the interstices between the filaments 36.

In use the heater assembly operates by resistive heating. Current is passed through the filaments 36 under the control of control electronics 16, to heat the filaments to within a desired temperature range. The mesh or array of filaments has a significantly higher electrical resistance than the electrical contacts 32 and electrical connectors 19 so that the high temperatures are localised to the filaments. The system may be configured to generate heat by providing electrical current to the heater assembly in response to a user puff or may be configured to generate heat continuously while the device is in an "on" state. Different materials for the filaments may be suitable for different systems. For example, in a continuously heated system, graphite filaments are suitable as they have a relatively low specific heat capacity and are compatible with low current heating. In a puff actuated system, in which heat is generated in short bursts using high current pulses, stainless steel filaments, having a high specific heat capacity may be more suitable.

In a puff actuated system, the device may include a puff sensor configured to detect when a user is drawing air through the mouthpiece portion. The puff sensor (not illustrated) is connected to the control electronics 16 and the control electronics 16 are configured to supply current to the heater assembly 30 only when it is determined that the user is puffing on the device. Any suitable air flow sensor may be used as a puff sensor, such as a microphone.

In a possible embodiment, changes in the resistivity of one or more of the filaments 36 or of the heater element as a whole may be used to detect a change in the temperature of the heater element. This can be used to regulate the power supplied to the heater element to ensure that it remains within a desired temperature range. Sudden changes in temperature may also be used as a means to detect changes in air flow past the heater element resulting from a user puffing on the system. One or more of the filaments may be dedicated temperature sensors and may be formed from a material having a suitable temperature coefficient of resistance for that purpose, such as an iron aluminium alloy, Ni—Cr, platinum, tungsten or alloy wire.

The air flow through the mouthpiece portion when the system is used is illustrated in FIG. 1D. The mouthpiece portion includes internal baffles 17, which are integrally moulded with the external walls of the mouthpiece portion and ensure that, as air is drawn from the inlets 13 to the outlet 15, it flows over the heater assembly 30 on the cartridge where aerosol-forming substrate is being vapourised. As the air passes the heater assembly, vapourised substrate is entrained in the airflow and cools to form an aerosol before exiting the outlet 15. Accordingly, in use, the aerosol-forming substrate passes through the heater assembly by passing through the interstices between the filaments 36, 37, 38 as it is vapourised.

Other cartridge designs incorporating a heater assembly in accordance with this disclosure can now be conceived by one of ordinary skill in the art. For example, the cartridge may include a mouthpiece portion, may include more than one heater assembly and may have any desired shape. Furthermore, a heater assembly in accordance with the disclosure may be used in systems of other types to those already described, such as humidifiers, air fresheners, and other aerosol-generating systems.

Figure 5:
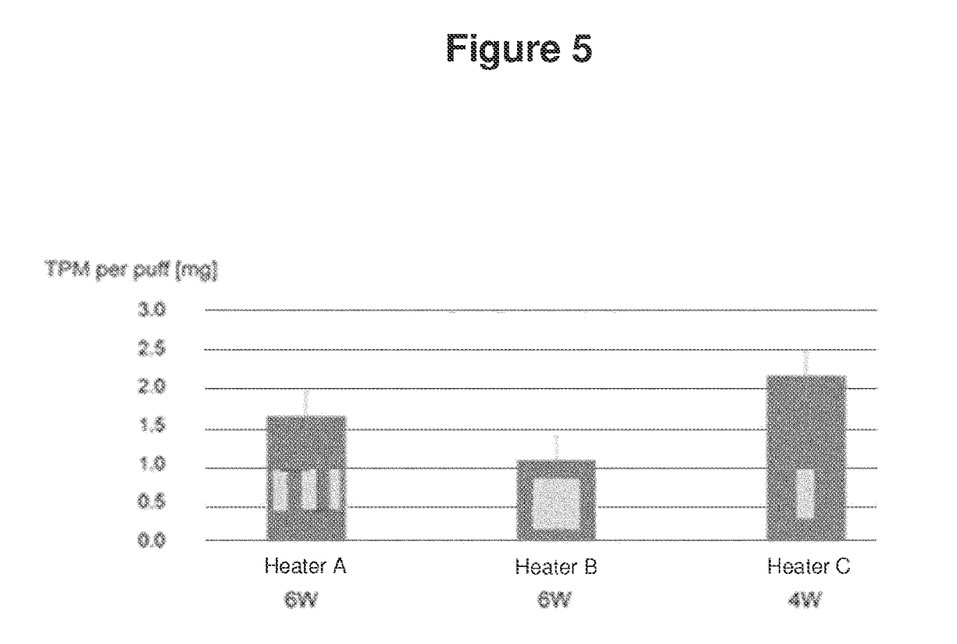
FIG. 5 is a diagram showing the TPM yield of different heater geometries.

FIG. 5 shows a diagram indicating the performance of three different configurations of heater elements in a test to measure the total particulate matter (TPM) deliveries provided by the example heating elements.

The heating elements tested were as follows:

Heater A—Aperture 5 mm×5 mm. Three heater elements arranged as for FIG. 3—each having a width of 1 mm. Approximate heater area 15 $mm^2$. Resistance approximately 1.2 Ohms. Power consumption 6 W.

Heater B—Aperture approximately 3 mm×3 mm. One heater element covering whole aperture. Approximate heater area 10 $mm^2$. Resistance approximately 0.5 Ohms. Power consumption 6 W.

Heater C—Aperture 5 mm×5 mm. One heater element arranged as for FIG. 2A, having a width of 2 mm. Approximate heater area 10 $mm^2$. Resistance approximately 0.8 Ohms. Power consumption 4 W.

A liquid-containing capillary material was mounted adjacent the heater. The liquid comprised by weight, 39% propylene glycol, 39% glycerine, 20% water, 2% nicotine.

A puff comprising an air flow of 55 ml per 3 seconds was passed over the heater during heating and the resulting aerosol entrained in the airflow is trapped on a fiberglass filter disc (Cambridge Pad). After the test run of 45 puffs, the aerosol components are extracted from the fiberglass filter disc using an alcohol solution in a known way to determine the total particulate matter (TPM) for that test run. The TPM per puff was calculated and is shown in FIG. 5.

Heater B including the heater element covering the whole aperture proved to have the lowest TPM yield (Total Particulate Matter) of only 1.1 milligramm per puff. The heater assembly had a power consumption of 6 Watts.

A higher TPM was observed with the heater C including only one 10 $mm^2$ heater element. With this heater assembly a TPM yield of about 2.2 milligramm per puff was achieved, while at the same time the power consumption only amounted to 4 Watts. Thus, a higher TPM was seen for a heater element of similar size to that of Heater B, even at lower power.

Without wishing to be bound by any particular theory, it is thought that for Heater C, where the edges of the heater are spaced from the aperture edge, there is less heat transfer to the substrate element. Also, it is thought that for heater B, some of the heat heats liquid underneath the substrate element and that that liquid is unable to be released through the aperture, thus leading to less efficient use of heat from the heater elements.

For Heater A including three heater strips, the TPM is also greater than for Heater B. Without wishing to be bound by any particular theory, TPM for Heater A may be lower than that for Heater C because the three 1 mm strips have a greater contact length with the edge of the aperture compared with the single 2 mm strip of Heater C which may lead to more heat transfer to the substrate or more ineffective heating of liquid underneath the substrate.

The exemplary embodiments described above illustrate but are not limiting. In view of the above discussed exemplary embodiments, other embodiments consistent with the above exemplary embodiments will now be apparent to one of ordinary skill in the art.

We claim:

1. An aerosol-generating system, comprising:
    an aerosol-generating device comprising a power source; and
    a cartridge removably coupled to the aerosol-generating device, the cartridge comprising:
        a liquid storage portion comprising a housing having an open end and containing a liquid aerosol-forming substrate,
        a heater assembly disposed at the open end of the housing and comprising a planar electrical heating element configured to heat the liquid aerosol-forming substrate to form an aerosol, and
        a capillary material disposed in contact with the planar electrical heating element and being configured to convey the liquid aerosol-forming substrate to the planar electrical heating element,
    wherein the liquid storage portion is disposed at a first side of the heater assembly and an airflow channel is disposed at a second side of the heater assembly, and
    wherein the power source of the aerosol-generating device is configured to supply power to the heater assembly.

2. The aerosol-generating system according to claim 1, wherein the planar electrical heating element comprises a planar substantially flat filament arrangement.

3. The aerosol-generating system according to claim 2, wherein the planar substantially flat filament arrangement extends in two directions.

4. The aerosol-generating system according to claim 2, wherein the planar substantially flat filament arrangement is one filament.

5. The aerosol-generating system according to claim 2, wherein an electrical resistance of an electrically conductive filament of the planar substantially flat filament arrangement is between 0.3 Ohms and 4 Ohms.

6. The aerosol-generating system according to claim 2, wherein an electrical resistance of an electrically conductive filament of the planar substantially flat filament arrangement is between 0.5 Ohms and 3 Ohms.

7. The aerosol-generating system according to claim 2, wherein an electrical resistance of an electrically conductive filament of the planar substantially flat filament arrangement is about 1 Ohm.

8. The aerosol-generating system according to claim 1, wherein the heater assembly further comprises a support having an aperture formed therein.

9. The aerosol-generating system according to claim 8, wherein the heater assembly further comprises a pair of electrical contacts fixed to the support.

10. The aerosol-generating system according to claim 9, wherein an electrical resistance of the planar electrical heating element is at least an order of magnitude greater than an electrical resistance of the electrical contacts connecting the planar electrical heating element to the power source.

11. The aerosol-generating system according to claim 9, wherein an electrical resistance of the planar electrical heating element is at least two orders of magnitude greater than an electrical resistance of the electrical contacts connecting the planar electrical heating element to the power source.

12. The aerosol-generating system according to claim 9, wherein the planar electrical heating element comprises at least one filament disposed between the pair of electrical contacts and respectively connected to ends of the at least one filament.

13. The aerosol-generating system according to claim 12, wherein the pair of electrical contacts are respectively bonded to the ends of the at least one filament.

14. The aerosol-generating system according to claim 1, wherein the heater assembly is configured to operate by resistive heating.

15. The aerosol-generating system according to claim 1, further comprising electric circuitry connected to the heater assembly and to the power source,
wherein the electric circuitry is configured to
monitor an electrical resistance of the heater assembly or of the planar electrical heating element, and
control a supply of power from the power source to the heater assembly dependent on the electrical resistance of the heater assembly or of the planar electrical heating element.

16. The aerosol-generating system according to claim 1, further comprising a plurality of air inlets and an air outlet.

17. The aerosol-generating system according to claim 1, wherein the aerosol-generating device comprises a main body, and
wherein the main body comprises a cavity configured to receive the cartridge.

18. The aerosol-generating system according to claim 17, wherein the cartridge further comprises first electrical connectors and the main body further comprises second electrical connectors, and
wherein the second electrical connectors are disposed within the cavity so as to make electrical contact with the first electrical connectors when the cartridge is disposed in the cavity.

19. The aerosol-generating system according to claim 17, wherein the cavity and the cartridge are shaped to ensure an electrical connection between the aerosol-generating device and the cartridge.

20. The aerosol-generating system according to claim 1 wherein the heater assembly has a width that is smaller than a width of the open end of the housing.

* * * * *